(12) United States Patent
Goeldner

(10) Patent No.: US 6,926,863 B1
(45) Date of Patent: Aug. 9, 2005

(54) METHOD AND DEVICE FOR TREATING CONTAMINATED MATERIALS

(76) Inventor: Helmut Goeldner, Gewerbegebiet Oehmer Feld, D-31633 Leese (DE)

( * ) Notice: Subject to any disclaimer, the term of this patent is extended or adjusted under 35 U.S.C. 154(b) by 0 days.

(21) Appl. No.: 09/744,297

(22) PCT Filed: Jul. 20, 1999

(86) PCT No.: PCT/DE99/02212
§ 371 (c)(1),
(2), (4) Date: Jan. 23, 2001

(87) PCT Pub. No.: WO00/04935
PCT Pub. Date: Feb. 3, 2000

(30) Foreign Application Priority Data

Jul. 23, 1998 (DE) .......................................... 198 33 024

(51) Int. Cl.[7] .............................. A61L 2/00; A61L 2/08; G05D 9/00; F28D 7/00; B09B 3/00
(52) U.S. Cl. ................................ 422/26; 422/1; 422/22; 422/106; 422/184.1; 422/186; 422/200; 422/308
(58) Field of Search ............................. 422/1, 5, 21–22, 422/24, 26–28, 31–33, 38, 65, 106, 184.1, 186, 188, 193, 195, 198, 200, 201–204, 295–298, 300, 304, 307–309, 905, 303

(56) References Cited

U.S. PATENT DOCUMENTS 5,217,688 A * 6/1993 Von Lersner
5,270,000 A * 12/1993 Goldner et al.
5,277,136 A * 1/1994 Davis
5,425,925 A * 6/1995 Kline et al.
5,455,005 A * 10/1995 Clawson et al.
5,487,873 A * 1/1996 Bridges et al.
5,656,248 A * 8/1997 Kline et al.
6,368,555 B1 * 4/2002 Goeldner

FOREIGN PATENT DOCUMENTS

DE 3938546 C 7/1990
DE 9213599.4 U * 8/1992 ........... A01G/11/00
DE 9213599.4 U 10/1992
DE 4409391 A1 3/1994

* cited by examiner

Primary Examiner—William H. Beisner
Assistant Examiner—Monzer R. Chorbaji
(74) Attorney, Agent, or Firm—Crowell & Moring LLP

(57) ABSTRACT

A method and apparatus (1) for treating contaminated materials in which the materials are fed by an input unit (2, 3, 4) to a conveyor system (9) extending through a treatment chamber (6) where they are heated, treated and discharged via a discharge element (12). A liquid reservoir (16) is created in a first treatment area of the treatment chamber (6) by inclining the treatment chamber. The first area is also heated to a temperature below the boiling point of water, and a second area extending from th first treatment area to the top end of the treatment chamber (6) is at least partially heated to a temperature above the boiling point of water. This enables the contaminated material to be treated and compacted in a simpler, more reliable manner and in a (quasi-) continuous flow through several treatment areas.

20 Claims, 2 Drawing Sheets

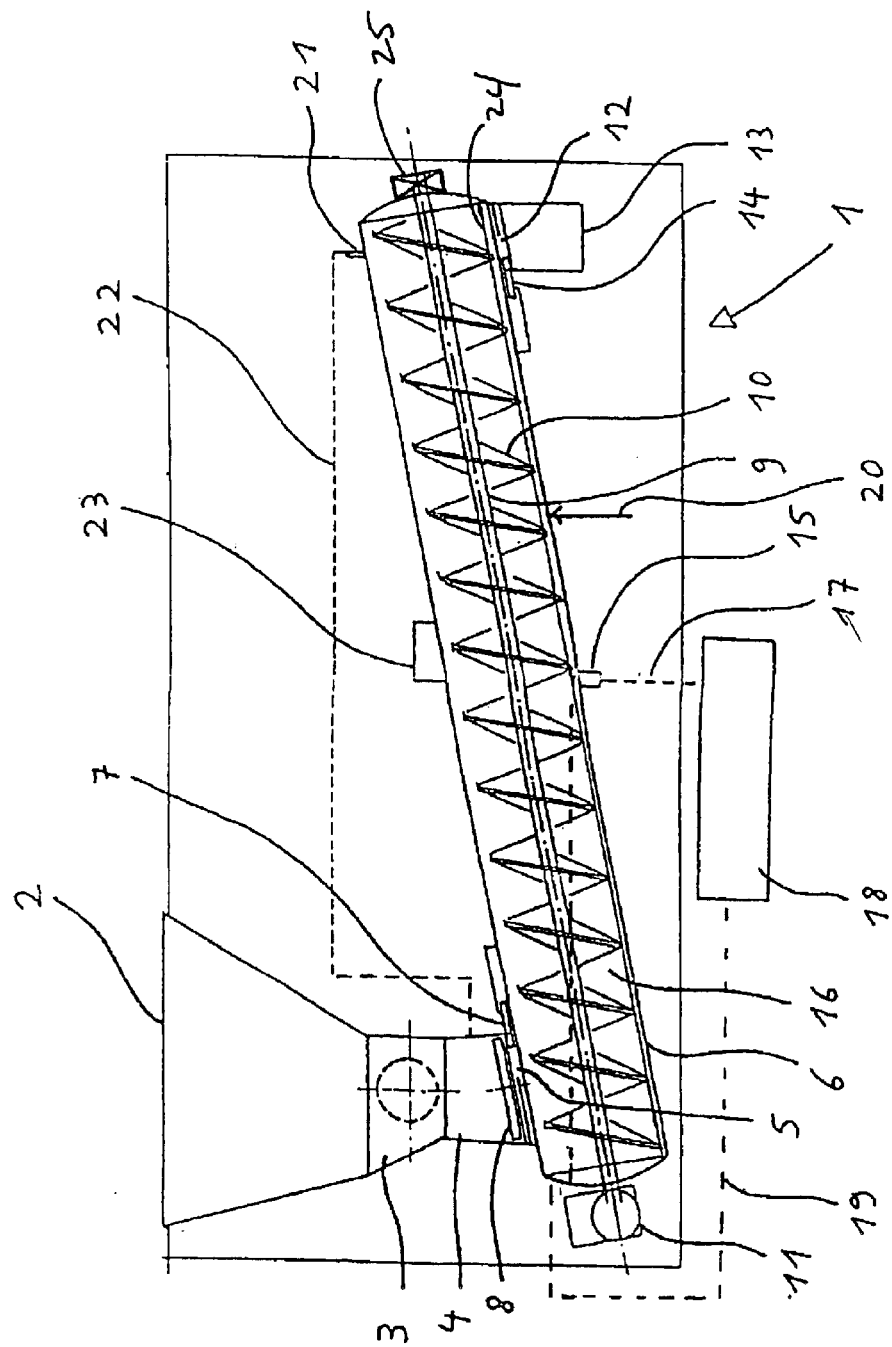

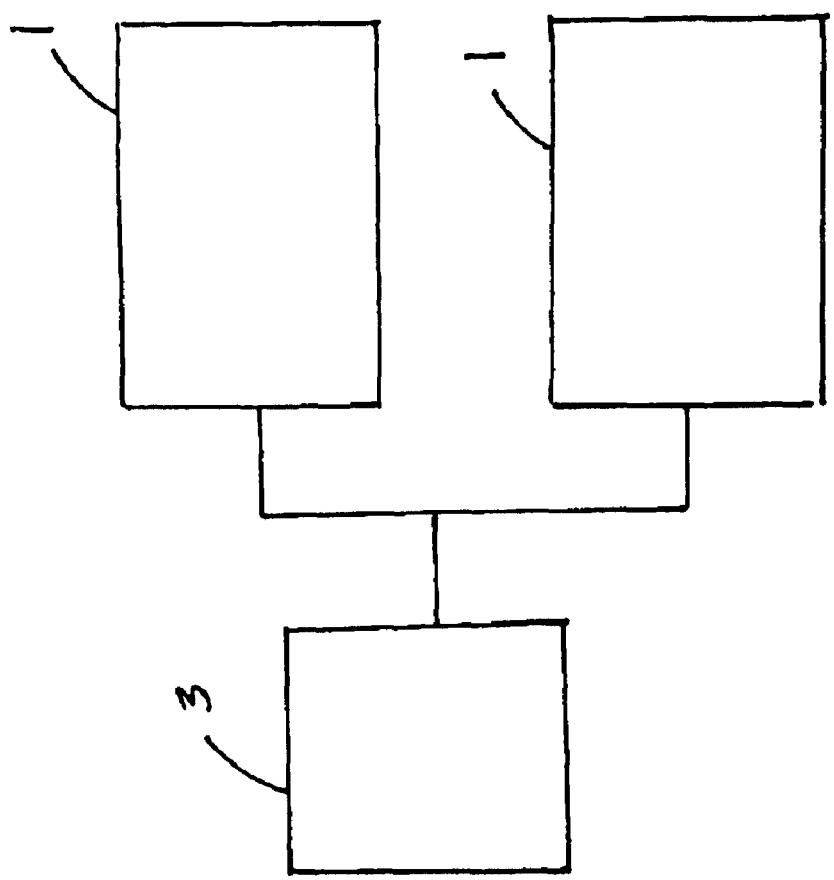

METHOD AND DEVICE FOR TREATING CONTAMINATED MATERIALS

BACKGROUND OF THE INVENTION

The invention concerns a method for the treatment of contaminated materials, particularly infected materials, whereby said materials are fed by means of an input unit to a conveyor system extending into a treatment chamber, where they are heated, treated, and discharged via a discharge element. Furthermore, the invention concerns a device for the above method in which essentially the entire treatment chamber is slanted upward in the direction of transport.

A high-temperature disinfection plant for hospital-specific waste is already known from DE 39 38 546 C2 in which the wastes are supplied to two screw segments separated by a mechanical pressure-sealed intermediate lock via a receiving hopper. An adjustable steam pressure is hereby generated in the first screw segment through the introduction of heat, while a partial vacuum is generated in the second screw segment in order to dehumidify the material by sucking away the steam. In this known plant, it is disadvantageous that the two screw sections are separated by a mechanical pressure lock which is expensive and, of course, also represents a potential source of defects. In addition, the screw sections are positioned in the horizontal plane in such a way that contaminated liquids can flow unnoticed through the plant and pass through the disinfection process untreated and/or insufficiently treated. It is in no way assured here that a safe disinfection and/or, in particular, sterilization of the wastes occurs.

A device for the regeneration and sterilization of soil is known from DE 92 13 599 U1. In this device, the soil is sent through a slanted treatment chamber and thereby impinged upon by steam. It is, however, disadvantageous in this device that two different treatment zones which serve for moistening and/or for disinfection or sterilization of the material to be treated are not provided. Rather, disinfection or sterilization occurs over the entire area of the treatment chamber. Furthermore, no pressure buildup can occur in the device because it is not a closed system.

A device and a method for the sterilization and disinfection of contaminated hospital waste is also already known from DE 41 38 938 A, in which the waste is first shredded and the damp granulate thus obtained is subsequently fed to a disinfection screw in a slanted treatment chamber, wherein three regions are provided for treatment. The granulate is first dried in the lower region and subsequently agitated and disinfected with flowing steam in the next section of the disinfection screw, which lies higher up, in order to finally be redried in the upper part of the disinfection screw and conveyed to a container via a conveyor device.

Furthermore, a method and a device for the decontamination of bulk material is described in DE 44 09 391 A1. However, in this prior art as well, two different treatment zones for moistening and/or for decontamination of the material are not provided. In addition, a closed system suitable for pressure buildup is not provided here, either.

SUMMARY OF THE INVENTION

It is the object of the invention to provide a method and a compact device which, using simple technical means, make possible different treatment zones for batch operation, single step and multi-step processes, and continuous operation, while always assuring a reliable disinfection and/or sterilization of contaminated materials.

This object is achieved in accordance with the invention as described and claimed hereinafter. The further development of the invention can be inferred from the following description.

In the method according to the invention, a first treatment zone for moistening of the infected materials is made by producing a liquid reservoir in a first region of the treatment chamber with the liquid present in the infected material and/or the introduction of water from the exterior by slanting essentially the entire treatment chamber upwards in the direction of transport and heating the liquid reservoir to a temperature lower than the boiling point of water, wherein the first region lies adjacent the lower end of the treatment chamber. Furthermore, a second treatment zone for disinfection and/or sterilization is made by heating a second region, extending from the first region up to the higher end of the treatment chamber, at least partially to a temperature higher than the boiling point of water and building up the steam pressure required for disinfection and/or sterilization in the second region.

In this way, it is assured that contaminated liquid always collects in a defined region of the treatment chamber and thereby cannot flow unnoticed into an undesired section of a device used. In addition, at least two treatment zones are created according to the method, namely a first one, in which the infected material is moistened within the liquid reservoir, and a second, in which the temperature and the steam pressure are provided which are necessary for disinfection or sterilization. The method allows a continuous and/or quasi-continuous disinfection and/or sterilization process, whereby the optimization of dwell times in the various treatment zones can be assured due to shorter paths.

It can be provided that the second region of the treatment chamber is divided into sections, each with a different temperature. Thus, for example, a section which borders immediately on the first region can have a lower temperature than the following section and thereby serve as a transition section. In this transition section steam, for example, can be supplied in order to achieve the desired steam pressure in the second region, in which the second step of the disinfection and/or sterilization process occurs. Furthermore, particularly in this transition section, various measurement procedures for determination of process parameters can be performed.

In the first region, means for the supply of water in liquid form can be provided in order to keep the level of the liquid reservoir at a preset height. The maximum level of the liquid reservoir is preferably regulated via an overflow. It is hereby practical if the liquid which flows into the overflow can be fed back into the liquid reservoir so that it can also be disinfected or sterilized at a later time in a separate process.

It can be provided that the material to be treated is supplied in small portions, whereby the supply and the removal occurs via slide valves and/or pressure locks of the input unit and the discharge element. The portions are hereby each at different treatment steps. By means of the locks it can be assured that no noticeable loss of pressure occurs during the feeding and/or the removal of batches, and the technical process parameters therefore do not change. A slight transient pressure variation can, however, also be intentional, in order to positively influence the effectiveness of the disinfection and/or sterilization process by such "breathing".

The conveyor system used in the method preferably has a screw conveyor.

In the method, the saturated steam desired in the second region of the treatment chamber can be produced merely by moving the material to be treated out of the liquid reservoir and, thus moistened, into the second region of the treatment chamber, where the water on the surface of the waste steams. As a rule, this inherent moisture of the material to be treated is sufficient to produce the steam pressure required. If, however, the steam pressure thus obtained is not sufficient, additional steam can be supplied.

The device according to the invention is characterized in that the treatment chamber has a first heating zone which lies adjacent the lower end of the treatment chamber and is designed to generate a temperature below the boiling point of water and, furthermore, has a second heating zone which extends between the first heating zone and the higher end of the treatment chamber and is designed to generate a temperature above the boiling point of water and to build up the steam pressure required for disinfection and/or sterilization.

Slanting the treatment chamber ensures that the liquid which is in the contaminated materials supplied to the treatment chamber and is, for example, released by the action of an upstream shredder collects in the first heating zone. This assures on one hand that contaminated liquid does not reach undesired regions of the treatment chamber. On the other hand, a liquid reservoir is produced through the collection of the contaminated liquid and, if necessary, through the external addition of water which can be used for moistening of the materials to be treated. The first heating zone is designed so that the liquid reservoir can be heated to a temperature which is slightly below the boiling point of water, i.e., under 100° C. at atmospheric pressure. Therefore, because the temperature is below the prevailing boiling point, a high evaporation rate of the water and undesired encrustations on the inner walls of the treatment chamber or on the conveyor system are prevented. In addition, because the boiling point is not attained, the release of vapors and possible odors when the input unit is opened is prevented. The device according to the invention makes the production of several temperature and/or treatment zones possible while requiring little space. Due to the technical means, a reliable hermetic shield, and thus reliably reproducible process control, is assured in which a very economical disinfection and/or sterilization can be performed.

The first heating zone can, for example, have means for the supply of liquid water so that the level of the liquid in the liquid reservoir can be regulated. The second step of the disinfection and/or sterilization method occurs in the second heating zone. The second heating zone can have means for the introduction of water in the form of liquid and of steam so that saturated steam can also be generated in case the inherent moisture of the material to be treated is not sufficient. In addition, means for the attachment of gauges of varying types, particularly temperature, dampness, and pressure gauges, as well as means for the supply of aggregates, can be provided in the second heating zone. In the framework of the invention it can be provided that the second heating zone is subdivided into further heating sections for the generation of further temperatures. Thus, for example, a section of the second heating zone bordering immediately on the first heating zone can represent a temperature transition from the first heating zone to a section of the second heating zone in which the temperature necessary for disinfection and/or sterilization is present.

Furthermore, it can be provided that the treatment chamber has an overflow for regulation of the liquid reservoir. This overflow preferably discharges into a pressure sealed collection vessel which is in turn connected with the treatment chamber through a return line. The overflow, the collection vessel, and the return line are preferably designed in such a way that they have the same pressure as in the treatment chamber. It is thus possible to pump liquid from the collection vessel into the treatment chamber through a simple pumping system if the liquid level in the treatment chamber is to be raised. An additional high-temperature disinfection and/or high-temperature sterilization unit can also be provided in which the liquid from the collection vessel can be treated. The collection vessel itself can hereby also be designed as an autoclave.

An array of heating means can be used to generate the respective temperatures in the different heating zones and/or heating sections. Thus, for example, the inner wall of the treatment chamber can be provided with heating means. This could consist of a double shell provided with heat transfer oil. The heat transfer oil is hereby heated by a heating block.

It can also be provided that microwave energy can be definably conducted into damp material in the treatment chamber and/or in the conveyor system in order to heat the material to the desired temperature.

The conveyor system preferably has a screw conveyor. This can be designed to be reversible in order, if necessary, to reduce pressure if a transport bottleneck occurs. It is advantageous if the screw conveyor only has a bearing on one end and rests on slide runners.

It is very practical if a shredder is positioned in the input unit, which is particularly advantageous for the shredding of contaminated hospital wastes.

To increase capacity, a plant can be provided which has several of the devices described above and one shredder unit, whereby the devices are laid out in parallel in such a way that they can be simultaneously and/or sequentially charged by the shredder unit. In this way, even if the individual devices are used in so-called batch operation, a quasi-continuous disinfection and/or sterilization can be performed.

BRIEF DESCRIPTION OF THE DRAWINGS

In the following, the device according to the invention will be described in more detail with the aid of an exemplary embodiment, whereby reference will be made to the Figures.

FIG. 1 schematically shows a device according to the invention.

FIG. 2 is a schematic of a parallel arrangement of the invention.

DETAILED DESCRIPTION OF PREFERRED EMBODIMENTS

In FIG. 1, a device for the treatment of contaminated materials, particularly infected materials, is indicated with 1. The device 1 has a feed hopper 2, under which a shredder 3 is positioned, as a component of an input unit. From the shredder 3, a gravity feed hopper 4 leads to an intake 5 of a tube-shaped treatment chamber 6. The intake 5 can be closed by a slide valve 7. In place of the slide valve 7, or in addition to same, a lock could also be provided. A metering device 8 is position above the intake 5.

A screw conveyor 9 having a conveyor spiral 10 extends into the treatment chamber 6. The screw conveyor 9 is driven by a drive 11 has a bearing 25 at one end, and rests on slide runners 24. The treatment chamber 6 is slanted upwards in the transport direction of the screw conveyor 9, with, for example, an angle to the horizontal of approximately 10° to 40°. The screw conveyor 9 can rest on slide runners 24. A bearing 25 is provided at only one end of screw conveyor 9. At the upper end of the treatment chamber 6 there is a discharge element 12 with a discharge chute 13. The discharge element 12 is also provided with a slide valve 14. A lock could, of course, also be provided here instead of the slide valve 14 or in addition to same.

An overflow 15 for liquid 16, which can collect in a lower region of the treatment chamber 6, is positioned on the lower side of the treatment chamber 6. The overflow 15 is connected via a conduit 17 with a collection vessel 18. The collection vessel 18 is connected via a further conduit 19 with the treatment chamber, whereby the conduit 19 discharges above the maximum level of the liquid 16 in the lower end of the treatment chamber 6.

The device 1 has two heating zones in which different temperatures can be generated. The first heating zone extends from the lower end of the treatment chamber 6 to the overflow 15. The second heating zone is immediately adjacent to the first heating zone and extends up to the upper end of the treatment chamber 6. In order to simplify the figure, the heating means of the two heating zones are not shown. They could, for example, be comprised of a double casing of the treatment chamber 6 filled with heat transfer oil, wherein the double casing has two chambers, corresponding to the two heating zones. The heat transfer oil is hereby, for example, heated by two separate heating blocks. It is also possible to use heat exchangers.

There is a ventilation valve 21 at the upper end of the treatment chamber 6 connected via a conduit 22 with the gravity feed hopper 4. Furthermore, inlet means 23 for the introduction of steam are provided in the second heating zone.

The metering device 6 is positioned over the intake 5, which is formed as a slot in a base plate and can be closed by the slide valve 7.

In order to treat contaminated materials, the material to be treated is supplied to the device 1 via the feed hopper 2. The shredder 3 shreds the material to a size of, for example, approximately 10×20 mm in cross-section, whereby in hospital wastes hollow bodies, such as syringes, are destroyed. The material is then supplied via the gravity feed hopper 4 to the metering device 8. The metering device 8 assures that the material reaches the intake 5 after shredding, without the occurrence of bridging within the intake 5. The truncated cone shape of the gravity feed hopper 4 also helps to prevent bridging.

The material to be treated reaches the liquid reservoir 16 in the treatment chamber 6. The liquid portion of the material to be treated released by the shredder 3 contributes to the liquid reservoir 16, whose liquid level is measured by a liquid sensor (not shown) and can, if necessary, be raised to the desired value by the supply of liquid from the collection vessel 18 or by the addition of liquid water. The liquid reservoir 16 has a temperature which is slightly lower than the prevailing boiling point of water. In this way, encrustations on the inner walls of the treatment chamber 6 or on the screw conveyor 9 are prevented. The material to be treated is soaked in the liquid reservoir 16. The material is subsequently transported into the second heating zone via the screw conveyor 9. This heating zone essentially, i.e., in a transition section of the second heating zone extending from the overflow 15 up to approximately the height of the treatment chamber 6 indicated by the arrow 20, has a temperature above the boiling point, so that the water of the moistened material steams and a corresponding steam pressure builds up. The process conditions are adjusted so that the material is heated for disinfection to a temperature of more than, for example, 100° C. and for sterilization to a temperature of at least 121° C. For this purpose, saturated steam is generated which, if the inherent moisture of the material is not sufficient, can also be generated by supplying steam via the intake means 23 of the treatment chamber 6. The actual disinfection and/or sterilization process, which can last, for example, for a period of at least 15 minutes, occurs in the second heating zone. After the treatment process is finished, the ventilation valve 21 is first opened in order to let off the steam pressure. The steam is hereby fed to the gravity feed hopper 4, in which further material to be treated is already present which will be preheated by the steam. Further dehumidification of the treated material simultaneously occurs in that water which is on the surface of the material or which clings to the material due to capillary action steams due to the reduction in pressure while utilizing the tangible heat of the material, while the temperature of the water and material approaches the boiling point at normal pressure. The discharge element 12 is subsequently opened by the slide valve 14 in order to remove the treated material. The intake 5 is preferably simultaneously opened in order to introduce further material to be treated into the treatment chamber 6 in proportion to the amount of material discharged.

If, instead of or addition to the slide valves 7 and 14, locks are provided, a continuous disinfection and/or sterilization process is also possible.

FIG. 2 shows an installation having several devices. The installation includes a shredder unit 3, whereby the devices 1 are positioned in parallel so that they can be supplied simultaneously and/or sequentially by the shredder unit 3.

With the device according to the invention, contaminated materials, which are preferably hospital-specific wastes, but could, for example, also be sewage sludge, contaminated soils, or foods, such as grains and spices, can be reliably disinfected and/or sterilized. The compact design of the device makes possible a cost-effective and reliable treatment of the materials and, in addition, the production of compact, efficient mobile plants.

What is claimed is:

1. A method for the treatment of contaminated material comprising feeding said contaminated material via an input unit to a conveyor system extending through a treatment chamber which slants upward in the conveyor transport direction and which comprises first treatment zone adjacent the lower end of the treatment chamber and second treatment zone extending from the first treatment zone to the upper end of the treatment chamber, and wherein said conveyor system comprises a screw conveyor and said screw conveyor has a bearing at only one end and rests on slide runners, heating and treating the contaminated materials in said treatment chamber, and discharging the treated materials via a discharge element, wherein said contaminated material is moistened in a liquid reservoir in said first treatment zone by liquid present in the contaminated material or water added from outside the treatment chamber, the liquid in said liquid reservoir being to a temperature lower than the boiling point of water, and thereafter heating the contaminated material in said second treatment zone at least partially to a temperature above the boiling point of water, wherein the input unit and discharge element are closed off, in order to build up steam pressure to disinfect the contaminated material.

2. A method according to claim 1, wherein said contaminated material is contaminated with infectious microorganisms.

3. A method according to claim 1, wherein the steam pressure in said second zone is generated by evaporation of the inherent moisture in the contaminated material.

4. A method according to claim 1, wherein the steam pressure in said second zone is generated by evaporation of liquid water added to the contaminated material from outside the treatment chamber.

5. A method according to claim 1, wherein the steam pressure in said second zone is generated by introducing steam into said treatment chamber.

6. A method according to claim 1, wherein the liquid level in said liquid reservoir is regulated by an overflow.

7. A method according to claim 6, wherein liquid discharged from said overflow is recycled back to the liquid reservoir.

8. A method according to claim 1, wherein the contaminated material to be treated is introduced in portions into the treatment chamber such that a plurality of portions are present in the treatment chamber at the same time, said portions being introduced into and discharged from the treatment chamber through slide valves or locks.

9. An apparatus for treating contaminated material, said apparatus comprising a treatment chamber which slants upward from a lower inlet end to an upper discharge end and which comprises first heating zone adjacent the lower end of the treatment chamber and a second heating zone extending from the first treatment zone to the upper end of the treatment chamber, an input unit and said inlet end for introducing contaminated material to be treated into the treatment chamber, a discharge element at said discharge end for discharging treated material from said treatment chamber, a conveyor system for conveying material to be treated through said treatment chamber, wherein said conveyor system comprises a screw conveyor, and said screw conveyor has a bearing at only one end and rests on slide runners, means for moistening contaminated material in said first heating zone, means for heating liquid in said first heating zone to a temperature below the boiling point of water, and means for heating moistened contaminated material in said second heating zone at least partially to a temperature above the boiling point of water, and means for closing off the input unit and the discharge element, to generate steam pressure to disinfect the contaminated material.

10. An apparatus according to claim 9, further comprising means for introducing steam into said second heating zone.

11. An apparatus according to claim 9, further comprising means for introducing liquid water into said first heating zone.

12. An apparatus according to claim 9, wherein said first treatment zone comprises a liquid reservoir, and further comprising an overflow for regulating the liquid level in said liquid reservoir.

13. An apparatus according to claim 12, further comprising a collection vessel which receives liquid from said overflow and a return line which connects said collection vessel to said treatment chamber for recycling liquid from said collection vessel back to said treatment chamber.

14. An apparatus according to claim 13, wherein said overflow, said collection vessel and said return line are maintained at the same pressure as said treatment chamber.

15. An apparatus according to claim 9, wherein at least one of said heating means is provided in an inner wall of said treatment chamber.

16. An apparatus according to claim 9, wherein at least one of said heating means is provided in said conveyor system.

17. An apparatus according to claim 9, comprising means for controlled introduction of microwave energy into said treatment chamber or said conveyor system.

18. An apparatus according to claim 9, further comprising a shredder in said input unit.

19. An apparatus according to claim 9, comprising slide valves or locks for opening and closing said input unit and said discharge element.

20. In combination, a shredder unit and a plurality of treating apparatus according to claim 9, said treating apparatus being arranged in parallel so that they can be supplied simultaneously or sequentially by the shredder unit.

* * * * *